(12) United States Patent
Levin et al.

(10) Patent No.: US 8,525,117 B2
(45) Date of Patent: Sep. 3, 2013

(54) OPTICAL DELAY COMBINING FOR MULTIPLEXING IN RADIATION IMAGING SYSTEMS

(75) Inventors: Craig S. Levin, Palo Alto, CA (US); Peter D. Olcott, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 217 days.

(21) Appl. No.: 12/798,679

(22) Filed: Apr. 8, 2010

(65) Prior Publication Data

US 2010/0258731 A1    Oct. 14, 2010

Related U.S. Application Data

(60) Provisional application No. 61/212,299, filed on Apr. 8, 2009.

(51) Int. Cl.
*G01T 1/164* (2006.01)

(52) U.S. Cl.
USPC ................. 250/363.03; 250/363.04; 250/369; 250/366

(58) Field of Classification Search
USPC ........... 250/363.06, 363.04, 366, 369, 363.03
See application file for complete search history.

(56) References Cited

U.S. PATENT DOCUMENTS

| | | | |
|---|---|---|---|
| 5,654,820 A | 8/1997 | Lu et al. | |
| 6,476,956 B1 * | 11/2002 | Cottrell et al. | 359/280 |
| 2004/0200966 A1 | 10/2004 | Ramsden | |
| 2008/0130857 A1 * | 6/2008 | Marwell et al. | 379/201.02 |
| 2009/0093710 A1 | 4/2009 | Levin et al. | |

FOREIGN PATENT DOCUMENTS

JP    08248140 A  *  9/1996

OTHER PUBLICATIONS

Paneque et al., "Analogue signal transmission by an optical fiber system for the camera of the Magic telescope", 2003, pp. 2927-2930, 28th Intl. Cosmic Ray Conference.
Pan et al., "Aligning microcavity resonances in silicon photonic-crystal slabs using laser-pumped thermal tuning", 2008, pp. 103114, Applied Physics Letters v92.
Butz et al., "Feasibility study of delay-line localization in a mini-PET scanner", 2001, pp. 695-698, Hyperfine Interactions v136/137.

* cited by examiner

*Primary Examiner* — Christine Sung
(74) *Attorney, Agent, or Firm* — Lumen Patent Firm

(57) ABSTRACT

Multiplexing for radiation imaging is provided by using optical delay combiners to provide distinct optical encoding for each detector channel. Each detector head provides an optical output which is encoded. The encoded optical signals can be optically combined to provide a single optical output for all of the detectors in the system. This single optical output can be coupled to a fast photodetector (e.g., a streak camera). The pulse readout from the photodetector can decode the arrival time of the event, the energy of the event, and which channels registered the detection event. Preferably, the detector heads provide coherent optical outputs, and the optical delay combiners are preferably implemented using photonic crystal technology to provide photonic integrated circuits including many delay combiners.

15 Claims, 4 Drawing Sheets

OPTICAL DELAY COMBINING FOR MULTIPLEXING IN RADIATION IMAGING SYSTEMS

CROSS REFERENCE TO RELATED APPLICATIONS

This application claims the benefit of U.S. provisional patent application 61/212,299, filed on Apr. 8, 2009, entitled "Coherent Optical Emission Imaging", and hereby incorporated by reference in its entirety.

FIELD OF THE INVENTION

This invention relates to multiplexing techniques for radiation imaging.

BACKGROUND

Medical imaging systems often make use of a large number of separate radiation detectors in order to provide high resolution imaging. For example, a typical positron emission tomography (PET) system may include hundreds or thousands of separate detectors. Furthermore, radiation imaging is often performed in conjunction with other imaging modalities (e.g., magnetic resonance imaging (MRI)) that can complicate the task of dealing with the large number of radiation detector channels. For example, MRI systems can generate significant levels of electrical interference. Accordingly, methods of multiplexing the detector channels, or otherwise reducing the cost/complexity of radiation imaging systems are of great interest.

One way to reduce the number of detector channels is considered in US 2004/0200966. In this work, a scintillation crystal array having M elements is coupled to a detector array having N<M elements. Each scintillation crystal is coupled to a distinct set of the detectors. As a result, the combination of detectors that provides signals in response to detected radiation serves to identify the relevant scintillation crystal. Although this approach reduces the number of electrical channels to less than the number of scintillation crystals, it can be difficult to achieve a large reduction of the number of channels in practice.

More specifically, it can be difficult to provide the required coupling of many scintillation crystals to each detector in practice. For example, 10 detectors in this approach could theoretically distinguish signals from about 1000 scintillation crystals. However, it would be necessary for each of the detectors to be connected to about 500 scintillation crystals, which presents substantial practical difficulties.

Accordingly, it would be an advance in the art to provide improved multiplexing for radiation imaging systems.

SUMMARY

Multiplexing for radiation imaging is provided by using optical delay combiners to provide distinct optical encoding for each detector channel. Each detector head provides an optical output which is encoded. The encoded optical signals can be optically combined to provide a single optical output for all of the detectors in the system. This single optical output can be coupled to a fast photodetector (e.g., a streak camera). The pulse readout from the photodetector can decode the arrival time of the event, the energy of the event, and determine which channels registered the detection event. Preferably, the detector heads provide coherent optical outputs, and the optical delay combiners are preferably implemented using photonic crystal technology to provide photonic integrated circuits including many delay combiners.

This approach provides several significant advantages. First, a very high degree of multiplexing can be obtained, which can greatly reduce overall system complexity. In particular, it is not necessary to have expensive fast electronics devoted to each channel separately, as is presently needed in conventional imaging systems. By only requiring expensive fast electronics in a single channel (i.e., at the combined optical output), highly significant cost reduction can be obtained compared to approaches that use hundreds or even thousands of channels of costly electronics in parallel. Second, the system front end is mostly or entirely optical, which reduces its vulnerability to electrical interference. Third, by having a single high performance channel, the timing resolution may be improved, which can improve image quality and accuracy (e.g., in time of flight PET (TOF-PET)).

DETAILED DESCRIPTION

Figure 1:
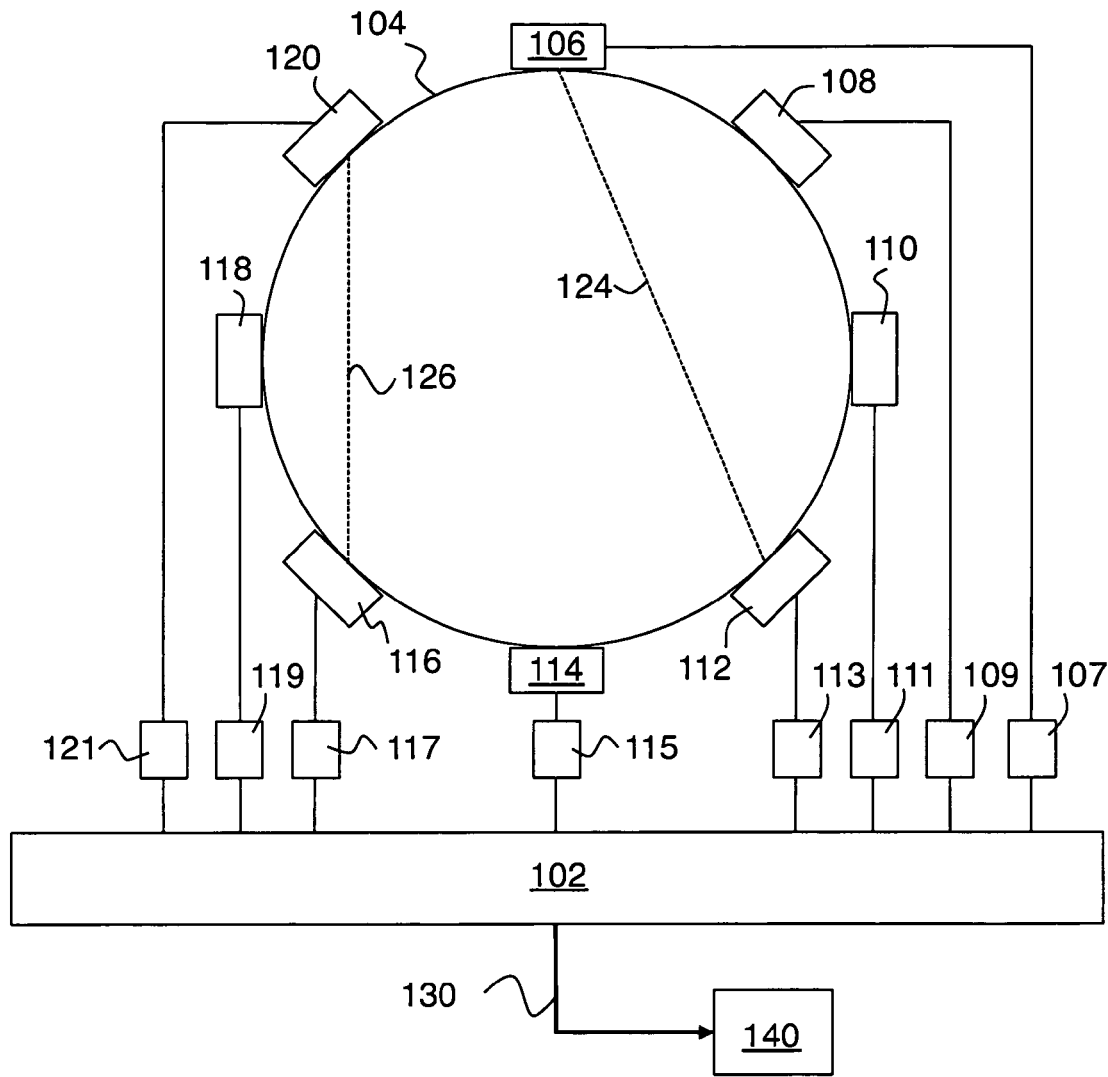
FIG. 1 shows a partial view of a system according to an embodiment of the invention.

FIG. 1 shows a partial view of a system according to an embodiment of the invention. In this example, radiation detector heads 106, 108, 110, 112, 114, 116, 118, 120 are disposed along a circumference 104 of a radiation imaging system. Each radiation detector head is capable of providing an optical output in response to received ionizing radiation. Ionizing radiation (e.g., X-rays, gamma rays) is radiation that is sufficiently energetic to ionize atoms or molecules by removing electrons. For simplicity, the example of FIG. 1 shows eight radiation detectors. Any number of detectors can be employed, and in practice the number of detectors is usually far larger than 8 (i.e., hundreds or thousands).

Each radiation detector head has a corresponding optical delay combiner. Optical delay combiner 107 corresponds to radiation detector head 106, as shown. Similarly, combiners 109, 111, 113, 115, 117, 119, and 121 correspond to radiation detector heads 108, 110, 112, 114, 116, 118, and 120 respectively. For ease of explanation, the optical delay combiners are shown as separate blocks from their corresponding detector heads on FIG. 1. It is also possible for the delay combiners to be integrated with the detector heads, such that each detector head assembly provides an optical output having delay encoding.

Each optical delay combiner has a distinct time delay. More specifically, an optical delay combiner is any device where input light is split into two or more paths, where the paths have different relative time delays, and where the paths are then combined into a single output. Optical delay combiners are regarded as having distinct time delays if the pattern of imposed relative time delays differs. For example, a 3-path combiner A having delays of 0, T1 and T2 and a 3-path combiner B having delays of 0, T1 and T3 have distinct delays if T2 and T3 are not equal. Continuing this example, a 3-path combiner C having delays T0, T1+T0 and T2+T0 is effectively the same as combiner A, so A and C do not have distinct time delays.

The optical delay combiners are connected to an optical multiplexer 102 which combines all optical delay combiner outputs to a single optical channel 130, if possible. More than one optical channel can be used, if needed. Optical channel 130 can be received by a fast photodetector 140 (e.g., a streak camera providing sub-ps time resolution), and the resulting signals can be processed electronically to recover detector position information, as described in greater detail below. Also, the time of the event is the time that the first pulse arrives at the detector. The energy of the event is the recovered integrated intensity of the optical signal.

Preferably, relative delays in the optical delay combiners are 2 ns or less, and can preferably be set with high accuracy and precision (e.g., with sub-ps resolution). This provides the capability of distinguishing a large number of channels. For systems having a large number of channels, the delay resolution of the system may be on the order of 0.1 ps (i.e., channels having a delay difference of 0.1 ps can be resolved to identify the pertinent channels).

It is also preferred to assign delays to the radiation detector heads in a systematic way according to the position of the detector heads. For example, if 2-path combiners are employed, the relative delays provided by combiners 107, 109, 111, 113, 115, 117, 119, and 121 could be T0, 2T0, 3T0, 4T0, 5T0, 6T0, 7T0, and 8T0, respectively.

This approach is applicable to any radiation imaging system or modality, including but not limited to: positron emission tomography (PET), time of flight PET (TOF-PET), single photon emission computed tomography (SPECT), gamma ray imaging, x-ray imaging, and X-ray computed tomography imaging. The present approach can be employed for medical imaging, or for any other radiation imaging application.

Figure 2:
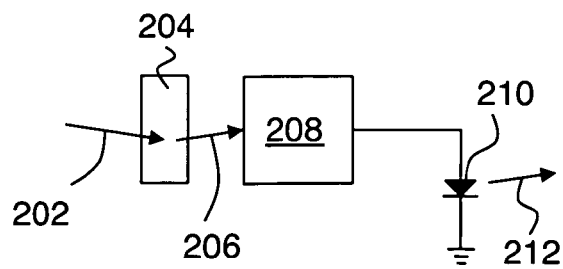
FIG. 2 shows an approach for providing optical output signals from radiation detector heads.

FIG. 2 shows a preferred approach for providing optical output signals from radiation detector heads. In this example, incident ionizing radiation 202 is received by a scintillation crystal 204, which emits optical radiation 206. Optical radiation 206 is received by a detector 208 (which can include driving circuitry such as an electronic amplifier), which provides a corresponding electrical signal to optical emitter 210 (e.g., a light emitting diode (LED) or laser diode), which emits optical radiation 212. Solid state photomultipliers are a preferred approach for the detector, although any kind of detector can be employed. Preferably, emitter 212 is fiber-coupled, such that optical radiation 212 is an optical signal on an optical fiber. In a preferred embodiment, emitter 212 is a vertical cavity surface emitting laser.

In a preferred embodiment, optical radiation 212 is self-coherent, and emitter 210 is a laser diode. A noteworthy feature of this embodiment is that radiation 206 emitted from scintillation crystal 204 is incoherent. Thus, detection followed by re-emission serves to convert incoherent optical radiation 206 to coherent optical radiation 212. In cases where the outputs of the detector heads are self-coherent optical outputs, the optical delay combiners can be regarded as being optical delay interferometers, since interference can occur in the combining.

It is also possible for the optical outputs of the detector heads to be incoherent. In this situation, the diagram of FIG. 2 can be simplified by omitting elements 208, 210, and 212, and directly using the scintillation crystal optical output 206 as the detector head output. However, the detect and re-emit approach of FIG. 2 may still be useful (e.g., if emitter 210 is a fiber-coupled LED).

Figure 3A:
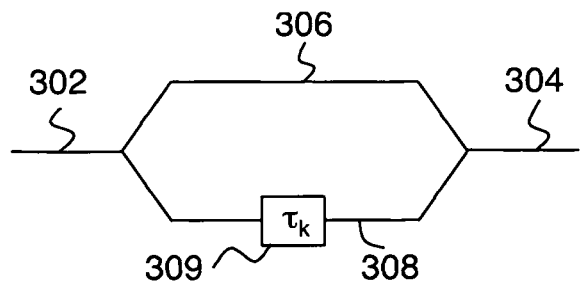
FIGS. 3a-b show exemplary optical delay combiners suitable for use in embodiments of the invention.
Figure 3B:
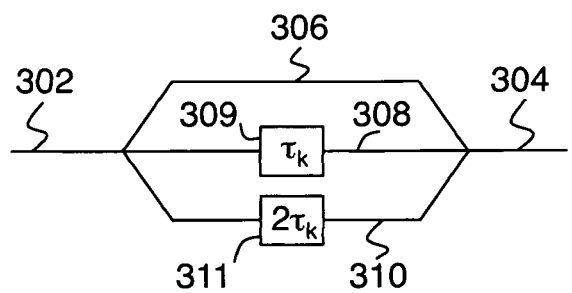

FIGS. 3a-b show exemplary optical delay combiners suitable for use in embodiments of the invention. The example of FIG. 3a is a 2-path combiner, where an optical input 302 is split into two paths 306 and 308 having a relative time delay 309 of $\tau_k$. Paths 306 and 308 are combined to provide the output 304. The example of FIG. 3b is a 3-path combiner which is similar to the example of FIG. 3a, except that a third path 310 having a relative time delay 311 of $2\tau_k$ is added. Here the index k refers to the corresponding detector head. Thus, in a system having N detectors, the delays $\tau_k$ are distinct for k=1, 2, ... N.

Figure 3C:
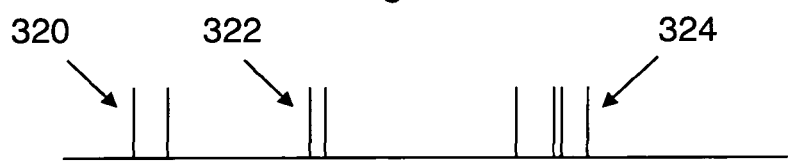
FIGS. 3c-e show exemplary pulse patterns relating to operation of embodiments of the invention.

The features of these exemplary combiners can best be appreciated by considering some simple examples of decoding at the combined optical output 130. First, we assume the use of 2-path combiners as in FIG. 3a for gamma ray imaging. In this situation, each single detection event will lead to two pulses on output 130 having a separation in time determined by the delay of the combiner corresponding to the detector head that provided the signal. For example, FIG. 3c shows single detection events 320 and 322, where the pulse separation in event 320 identifies the detector of event 320, and the pulse separation in event 322 identifies the detector of event 322. In cases where the pulses from separate detection events do not overlap in time, it is possible to identify the detector that provided each pair of pulses by determining the time separation of the pulses in the pair. If pulses from separate detection events overlap in time (e.g., as in 324 on FIG. 3c), the data is bad and no identification of the corresponding detector is possible. In order to reduce the fraction of data that is bad, it is preferred for the time delays of the combiners to be substantially less than the mean time between detection events, which is a condition that can readily be obtained in practice.

Next, we consider the use of 2-path combiners in connection with positron emission tomography (PET). In PET, the individual events of interest are positron annihilation events which lead to the simultaneous emission of two gamma rays in opposite directions. Thus, a PET detection event shows up as two detector signals, where it can be assumed the positron annihilation event occurred on the line of response (LOR) connecting the detectors. For example, if FIG. 1 is regarded as showing part of a PET system, simultaneous or near-simultaneous signals at detectors 116 and 120 indicate an annihilation on LOR 126, and simultaneous or near-simultaneous signals at detectors 106 and 112 indicate an annihilation on LOR 112.

Figure 3D:
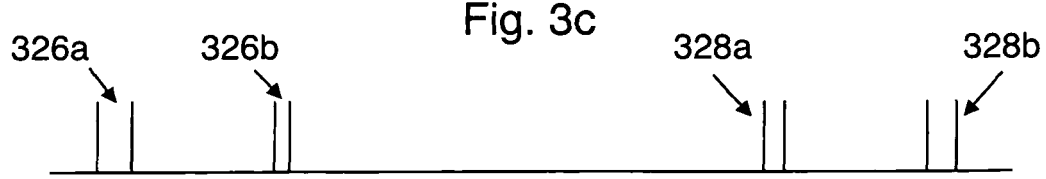

Thus, when 2-path combiners are used to provide optical delay encoding in connection with a PET system, the data of interest shows up as clusters of 4 pulses on output 130, where a first pulse pair has a delay that identifies the first detector of the LOR, a second pulse pair has a delay that identifies the second detector on the LOR, and the separation between the pulse pairs provides time of flight information for the LOR. FIG. 3d shows some examples. Here a first PET event gives rise to pulse pairs 326a and 326b. The separation of the pulses in pulse pair 326a identifies one of the corresponding detectors. Similarly, the separation of the pulses in pulse pair 326b identifies the other corresponding detector. With both detectors identified, the line of response is known. The separation between pulse pairs 326a and 326b relates to the position of the PET event on its line of response. For example, if the PET event were on the center of the line of response, the times of flight would be equal, and the pulse pairs would overlap. A similar analysis can be applied to pulse pairs 328a and 328b.

It is important to note that the typical time of flight across a medical imaging system is on the order of 2-3 ns. Thus, if delay encoding is performed with sub ns delays, and more preferably is performed with delays much less 1 ns (e.g., 10 ps or less), only a small fraction of the LOR will give rise to bad data caused by pulse pattern overlap. This time of flight also defines the coincidence window employed to identify PET events. More specifically, the gamma rays for a PET event are emitted simultaneously, but may not arrive at the detectors simultaneously due to differing times of flight. Thus, if two signals arrive at detectors within 2-3 ns of each other, they can be assumed to be from a single PET event, while signals that are isolated from other signals by more than 3 ns are assumed to be single detection events (e.g., as in FIG. 3c) and would be discarded in PET signal processing. As a final point, time of flight from the detector heads to multiplexer 102 for each channel should be matched to a precision of substantially better than 1 ns, in order to properly preserve PET coincidence information. However, it is important that it is not necessary to match these times of flight to a precision comparable to or better than the precision of the time delays in the optical delay combiners.

Figure 3E:

If a three path combiner is employed, the combined optical output signal for a PET event is a cluster of six pulses. FIG. 3e shows some examples, where pulse pairs 330a and 330b relate to one PET event and pulse pairs 332a and 332b relate to a second PET event. The use of three path combiners can reduce the amount of data that needs to be discarded as bad data because of pulse overlap. With patterns of three pulses, it is possible in some cases to identify the pulses of separate pulse patterns, even if the patterns overlap in time. When this is possible, these overlapping pulses can be processed normally, and do not need to be discarded as bad data.

Figure 4:
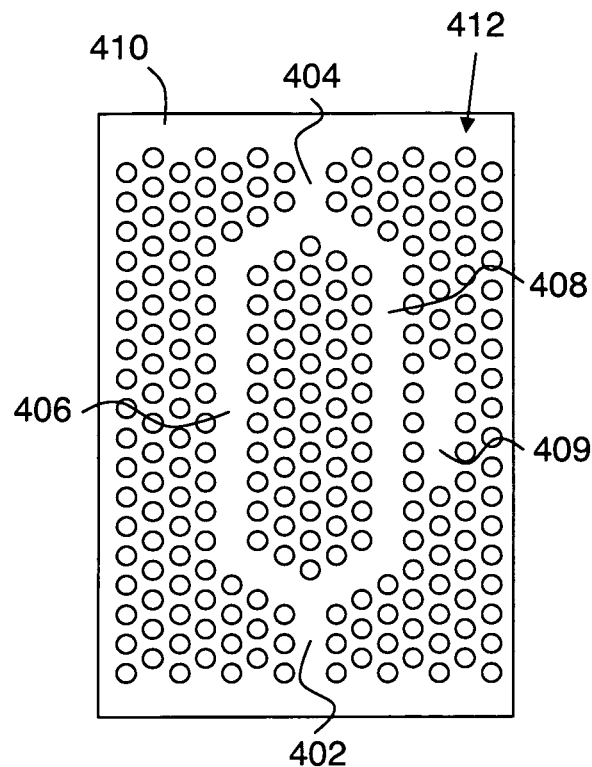
FIG. 4 shows a presently preferred approach for providing optical delay combiners.

FIG. 4 shows a presently preferred approach for providing optical delay combiners. In this example, a semiconductor device 410 includes a photonic crystal structure 412. Features are formed in the photonic crystal structure to guide and control optical signals. More specifically, an optical input waveguide 402 is split into two waveguides 406 and 408. An optical resonator 409 is disposed near (and optically coupled to) optical waveguide 408, and can provide an adjustable time delay for light propagating in waveguide 408. Waveguides 406 and 408 are combined to provide an output 404. Further details relating to this technology are described by Pan et al. ("Aligning microcavity resonances in silicon photonic-crystal slabs using laser-pumped thermal tuning", Applied Physics Letters v92, 103114, 2008, hereby incorporated by reference in its entirety). Although photonic crystal structures as in FIG. 4 are a presently preferred approach for providing the optical delay combiners, any other approach for implementing these components can also be employed in embodiments of the invention. One such example are different lengths of optical fiber and a 2:1 fiber combiner.

Figure 5:
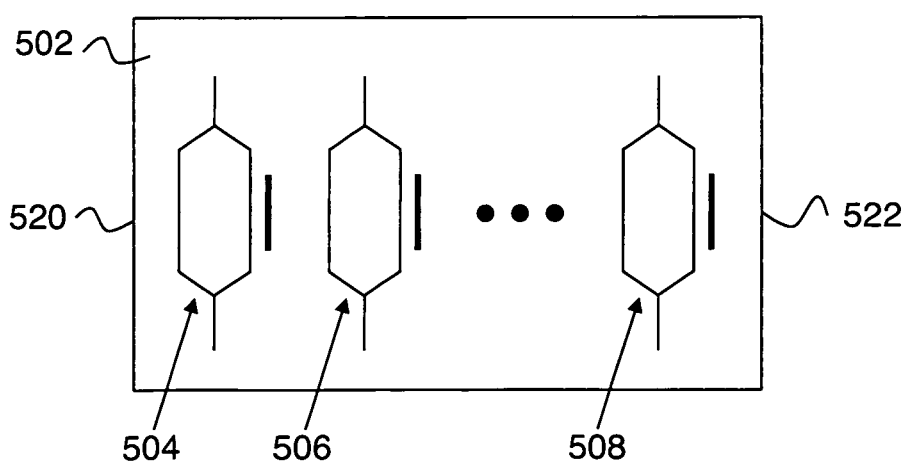
FIG. 5 shows a photonic chip including several optical delay combiners.

FIG. 5 shows a photonic chip including several optical delay combiners. In this example, a chip 502 includes combiners 504, 506, and 508 (and possibly many more, not shown). These combiners can be photonic crystal combiners, as in the example of FIG. 4. The time delays of such combiners are temperature tunable. Therefore, an array of combiners each having a different delay can be created by establishing a temperature gradient across chip 502. For example, a heat source can be disposed at a first edge 520 of chip 502, and a heat sink can be disposed at a second edge 522 of chip 502. In principle, such a chip could include all of the delay combiners for an entire imaging system. However, it is more likely that several chips would be used, each chip having some number of combiners that provides a reasonable balance between degree of integration and cost/yield.

The example of FIG. 5 shows complete integration of delay combiners, in the sense that several complete combiners are included on a single chip. It is also possible for a chip to include components of several optical delay combiners, which can be referred to as partial integration of the optical delay combiners. For example, a photonic chip can include an array of waveguides each having a tunable delay, and this chip can be used as part of several optical delay combiners by having the components for splitting and combining be off-chip.

Figure 6A:
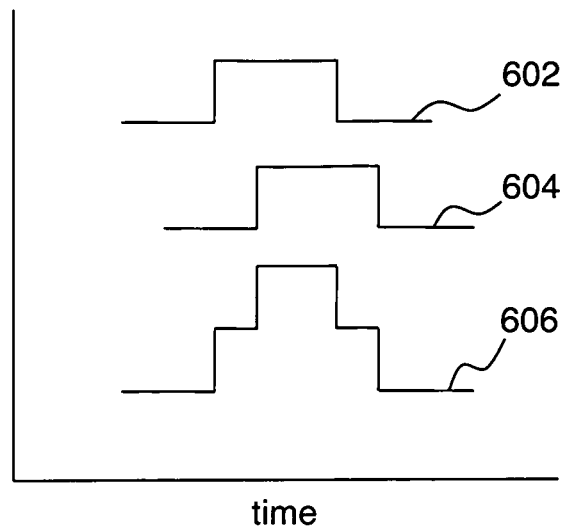
FIGS. 6a-b shows effects of in-phase and out-of-phase coherent optical combining.
Figure 6B:
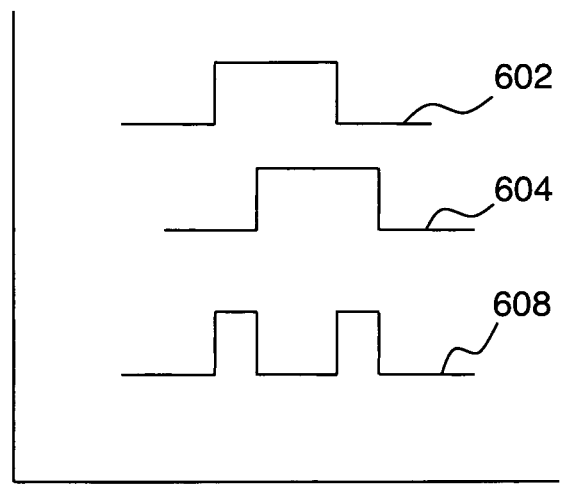

As indicated above, it is preferred for the radiation detector heads to provide coherent optical outputs. One reason for this preference is that coherent light can be more readily coupled to single mode waveguides/fibers, which advantageously reduces optical noise compared to the use of multi-mode waveguides/fibers. Another reason for this preference is that the use of coherent optical signals can facilitate time resolution to better than the width of the pulses. More specifically, FIGS. 6a-b shows effects of in-phase and out-of-phase coherent optical combining. In the in-phase example of FIG. 6a, a pulse 602 and a delayed pulse 604 are combined in-phase in the combiner, which gives a resulting combiner output pulse as in 606. In the out-of-phase example (i.e., 180° relative phase shift) of FIG. 6b, the combiner output pulse 608 becomes two narrow pulses due to destructive interference at times when pulses 602 and 604 overlap. Recognition of patterns as in 606 and especially 608 can provide sub-pulse width time resolution.

The invention claimed is:

1. A radiation imaging apparatus comprising:
   a plurality of radiation detector heads, wherein each of said radiation detector heads is capable of providing an optical output signal in response to received ionizing radiation;
   a plurality of optical delay combiners, wherein each of said radiation detector heads has its output connected to a corresponding one of said optical delay combiners, and wherein said optical delay combiners have distinct time delays; and
   an optical multiplexer configured to combine outputs from the optical delay combiners to a single optical channel;
   wherein said radiation detector heads each comprise a scintillation crystal to detect said ionizing radiation, an optical detector to detect incoherent light emitted from said scintillation crystal, and an optical output driver circuit that drives a laser diode in response to said optical detector.

2. The apparatus of claim 1, wherein said optical delay combiners each comprise a photonic crystal structure having a waveguide coupled to an optical resonator.

3. The apparatus of claim 2, wherein said optical delay combiners have a time delay that is tunable by varying temperature.

4. The apparatus of claim 3, wherein some or all of said optical delay combiners are partially or completely integrated onto a photonic chip, and wherein said photonic chip is configured to provide multiple distinct time delays by establishing a temperature gradient across said photonic chip.

5. The apparatus of claim 1 wherein said laser diode is a vertical cavity surface emitting laser.

6. The apparatus of claim 1, wherein relative delays of said optical delay combiners are 2 ns or less.

7. The apparatus of claim 1, wherein at least one of said optical delay combiners has three or more paths with distinct time delays.

8. The apparatus of claim 1, wherein said optical output signals are incoherent.

9. The apparatus of claim 1, wherein said optical output signals are self-coherent.

10. The apparatus of claim 9, wherein at least one of said optical delay combiners has two paths that are nominally combined with a phase shift of about 0°.

11. The apparatus of claim 9, wherein at least one of said optical delay combiners has two paths that are nominally combined with a phase shift of about 180°.

12. The apparatus of claim 1, wherein said optical delay combiners are delay interferometers.

13. The apparatus of claim 1, wherein delays are assigned to said radiation detector heads systematically according to position of said radiation detector heads.

14. A medical imaging system including the apparatus of claim 1.

15. The system of claim 14, wherein said medical imaging system comprises a system having an imaging modality selected from the group consisting of: positron emission tomography, time of flight PET (TOF-PET), single photon emission computed tomography, gamma ray imaging, x-ray imaging, and X-ray computed tomography imaging.

* * * * *